United States Patent [19]

Chastrette et al.

[11] Patent Number: 4,556,718

[45] Date of Patent: Dec. 3, 1985

[54] 4,5-DIALKOXY-1,3-DIOXOLANE-2-CARBOXYLIC ACIDS, THEIR DERIVATIVES, PREPARATION PROCESS AND APPLICATION

[75] Inventors: Francine Chastrette; Corinne Bracoud; Maurice Chastrette, all of Caluire, France

[73] Assignee: Societe Francaise Hoechst, Puteaux, France

[21] Appl. No.: 668,854

[22] Filed: Nov. 6, 1984

[30] Foreign Application Priority Data

Nov. 18, 1983 [FR] France .................. 83 18374

[51] Int. Cl.$^4$ ........................................... C07D 317/00
[52] U.S. Cl. .................................................... 549/449
[58] Field of Search ....................................... 549/449

[56] References Cited

U.S. PATENT DOCUMENTS

3,862,959  1/1975  Kirby et al. .................. 549/450

OTHER PUBLICATIONS

Kliegman et al., Journ. Org. Chem. 38(3), pp. 556–560.

Primary Examiner—Ethel G. Love
Attorney, Agent, or Firm—Karl W. Flocks; Sheridan Neimark

[57] ABSTRACT

The invention concerns new products of the general formula (I):

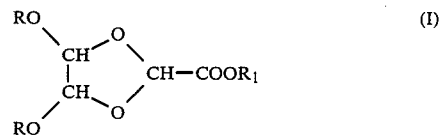

in which R represents an alkyl radical containing from 1 to 4 carbon atoms and $R_1$ is selected from the group comprising a hydrogen atom, and alkyl radicals containing from 1 to 4 carbon atoms, in their racemic and optically active forms, as well as the alkaline, alkaline-earth and amine salts, products having the general formula (I) in which $R_1$ represents a hydrogen atom, said products being capable of releasing glyoxal and products of the formula OHC—COOR$_1$ in which $R_1$ represents hydrogen or a $C_1$-$C_4$ alkyl radical.

8 Claims, No Drawings

4,5-DIALKOXY-1,3-DIOXOLANE-2-CARBOXYLIC ACIDS, THEIR DERIVATIVES, PREPARATION PROCESS AND APPLICATION

This invention relates to novel derivatives of 4,5-dialkoxy-1,3-dioxolane-2-carboxylic acid, their process of preparation and their application.

The object of this invention is the products having the general formula (I):

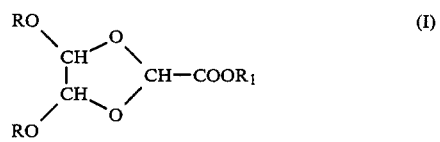

in which R represents an alkyl radical containing from 1 to 4 carbon atoms and $R_1$ represents a hydrogen atom or an alkyl radical containing from 1 to 4 carbon atoms, as well as the alkaline, alkaline-earth or amine salts of the products having the general formula (I) in which $R_1$ represents a hydrogen atom.

The term "alkyl" containing from 1 to 4 carbon atoms" may designate for example a methyl, ethyl, propyl, butyl radical.

The alkaline or alkaline-earth salts of the products having the general formul (I) in which $R_1$ represents a hydrogen atom can be for example the sodium, potassium, lithium, calcium or baryum salts.

The amine salts of the products having the formula (I) in which $R_1$ represents a hydrogen atom are the conventional amine salts. From the conventional amines, there can be cited monoalkylamines such as methylamine, ethylamine, dialkylamines such as dimethylamine, diethylamine, trialkylamines such as triethylamine. There can also be cited piperidine, morpholine.

The object of this invention is more particularly the products such as defined above characterized in that in formula (I) R represents a methyl or ethyl group and $R_1$ represents a hydrogen atom or a methyl or ethyl group in their racemic and optically active forms, as well as the alkaline salts, alkaline-earth salts or amine salts of said products having the formula (I) in which $R_1$ represents a hydrogen atom.

The object of this invention is more especially the following as novel industrial products:
methyl-4,5-dimethoxy-1,3-dioxolane-2-carboxylate,
ethyl-4,5-diethoxy-1,3-dioxolane-2-carboxylate,
4,5-dimethoxy-1,3-dioxolane-2-carboxylic acid,
4,5-diethoxy-1,3-dioxolane-2-carboxylic acid.

According to the invention, the products having the formula (I) above and their salts can be prepared by a process characterized in that glyoxylic acid is reacted with an equimolecular quantity of glyoxal in the presence of an alkanol having the formula ROH in which R represents a $C_1$–$C_4$-alkyl radical to obtain a product having the formula (I) in which R and $R_1$, identical, represent a $C_1$–$C_4$-alkyl radical, said product being hydrolyzed, if desired, at alkaline pH according to the conventional methods to obtain a product having the formula (I) in which R represents a $C_1$–$C_4$-alkyl radical and $R_1$ represents a hydrogen atom, said product being salified or esterified if desired in a neutral or alkaline medium according to conventional methods.

In preferred conditions for carrying out the invention, the above-described process is realized by hot reacting in acid medium glyoxylic acid with an equimolecular quantity of glyoxal in the presence of an alkanol, possibly in excess, having the formula ROH with removal in continuous manner of the reactional medium from the water formed either by azeotropic distillation after addition into said medium of one third of solvent capable of furnishing with water an azeotrope having a boiling point lower than 120° C. such as benzene or by any other known means.

Although the reactional medium is acid, due to the presence of glyoxylic acid it is however advantageous to work in the presence of catalytic quantities of a strong non valatile acid having a pKa lower than 1 such as paratoluenesulfonic acid.

The reaction is easily followed by controlling the water formed, then eliminated, and when the theoretical quantity of water calculated relative to the starting glyoxal is collected, the reactional medium is cooled then treatments are effected, consisting of removing the solution and eliminating the acid products by washing the reactional medium dissolved in an adequate solvent such as dichloromethane with an aqueous solution saturated with sodium bicarbonate. The desired product is then isolated by means known in themselves such as distillation.

In accordance with the invention, the products having the formula (I) above, in which R represents $C_1$–$C_4$-alkyl radical and $R_1$ represents a hydrogen atom, can be prepared by alkaline hydrolysis of the above products having the formula (I) in which R and $R_1$ represent a $C_1$–$C_4$-alkyl radical. In preferred conditions of process, such alkaline hydrolysis is realized in water in the presence of an excess of an alkaline metal hydroxide such as sodium hydroxide or potassium hydroxide.

The acid desired is isolated by means known in themselves, one of the simplest means of which consists of eliminating from the reactional medium the non salified products by washing with appropriate solvent such as ethyl oxide, then acidifying the aqueous phase to pH=1, and then extracting the acid desired with an adequate solvent.

Finally, the desired acid is isolated by distillation under vacuum of the extraction solvent. If necessary, such acid can be purified by recrystallization.

The alkaline, earth-alkaline or amine salts of products having the formula (I) in which R represents a $C_1$–$C_4$-alkyl radical and $R_1$ represents a hydrogen atom can be prepared by a conventional process such as for example by the action upon said acid products having the formula (I) of the corresponding bases or by reaction of double decomposition.

The salification reaction is effected preferably in a solvent or a mixture of solvent such as water.

The products of formula (I) in which R represents a $C_1$–$C_4$-alkyl radical and $R_1$ represents a hydrogen atom can be esterified into products having the formula (I) in which R and $R_1$ represent a $C_1$–$C_4$-alkyl radical by any known conventional methods for this type of carboxylic acids unstable in acid medium. Such known methods are for example esterification by diazomethane, the action of an alkyl halide on the sodium salt or the silver salt of said acid.

The products having the general formula (I) above under the different possible stereoisomeric forms as well as the alkaline and alkaline-earth or amine salts of said products having the formula (I) in which R represents a $C_1$–$C_4$-alkyl radical and $R_1$ a hydrogen atom, are interesting products in organic synthesis capable of supplying in an original form glyoxal and glyoxylic acid free or esterified having the general formula (II):

OHC—COOR₁                (II)

in which $R_1$ represents a hydrogen atom or a $C_1$-$C_4$-alkyl radical. As a matter of fact, such products according to the invention have a dioxolane ring stable in aqueous alkaline medium. On the other hand, in aqueous acid medium they quickly and quantitatively cleave releasing equimolar quantities of glyoxal and glyoxylic acid free or esterified having the general formula (II). Therefore, they constitute a masked source of glyoxal and glyoxylic acid free or esterified having the general formula (II) able to release in acid aqueous medium glyoxal and glyoxylic acid free or esterified mainly usable as known agents or reticulation of various substrates.

The above Examples illustrate the invention without however limiting it. The nuclear magnetic resonance spectra have been set up in the deuterated chloroform. The chemical displacements δ are expressed in ppm relative to silane tetramethyl used as an internal reference. The NMR¹H spectra have been effected on a VARIAN apparatus at 60 MHz and the NMR¹³C spectra on a VARIAN apparatus XL 100 A at 25.2 MHz with Fourier's transform. The mass spectra have been effected on an apparatus VARIAN Mat CH5 at 70 eV.

EXAMPLE 1

In a three-necked flask of 1 liter equipped for magnetic stirring and a vacuum distillation system there is disposed:

49.3 g (0.333 mole) of glyoxylic acid at 50% by weight in water;

48.4 g (0.333 mole) of glyoxal at 40% by weight in water.

This solution is thereafter heated under vacuum at a temperature lower than 50° C. up to removal of about 47 g of water i.e. about 88% of the initially present water.

Then, there is introduced into the reactional medium cooled to the ambient temperature:

265 g of benzene;

79 g (1.71 mole) of ethanol.

There is substituted for the vacuum distillation system a reflux refrigerant provided with a Dean Stark apparatus, then the reactional solution is heated for 4 hours with reflux by collecting 20 cm³ of ternary azeotrope: water-ethanol-benzene.

At this stage, there is introduced into the reactional solution:

16 g (0.34 mole) of ethanol;

2.5 g (13 mmoles) of monohydrated paratoluenesulfonic acid;

then the reflux is continued by eliminating as previously the water formed, by azeotropic distillation. After 12 hours of reflux, no more water is drained and analysis of a test sample of vapor phase chromatography on a column Ucon Polar at 15% by weight of Chromosorb W 80-100 shows that the reaction no longer evolves. Thus, there is collected a total of 19.4 g (1.08 mole) of water.

Benzene and ethanol are removed under vacuum, then the residual oil is dissolved in dichloromethane. Such solution is thereafter washed with an aqueous solution saturated with sodium bicarbonate up to complete elimination of its acid constituents, and then with salted water up to neutral washings. The organic dichloromethylenic phase is then dried on anhydrous magnesium sulfate, filtered, thereafter the extraction solvent is removed under vacuum. Thus, there is isolated 90 g of yellow oil which is separated into two fractions by distillation under vacuum of a 24 mbars:

a first fraction A of 37 g passing at a temperature lower than or equal to 90° C.;

a second residual fraction B of 53 g.

A vapor phase chromatographic analysis realized on a column with silicones at 10% by weight shows that the first fraction mainly consists of monomeric acetals of the ethyl glyoxylate, 1, and of glyoxal, 2:

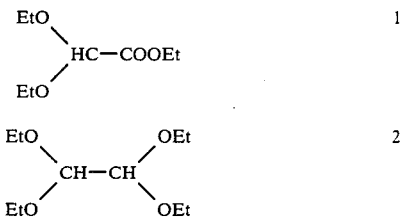

which are respectively described in the literature in Beil.3, 601; 3, I, 210; 3, II, 389; 3, III, 1139, $E_{14}$=84°-85° C., and by Jonathan M.KLIEGMAN et al., J.Org.Chem., 1973, 38, 556-560 and 1972, 37, 1276-1279, $E_{10}$=84°-85° C.

The second fraction contains by weight:

49% of ethyl-4,5-diethoxy-1,3-dioxolane-2-carboxylate, (3);

21% of 4,5-diethoxy-2-diethoxymethyl-1,3-dioxolane, 4, described in the literature by J.M.KLIEGMAN, loc.cit., $Eb_4$=120°-121° C.

28% of a mixture of products, C.

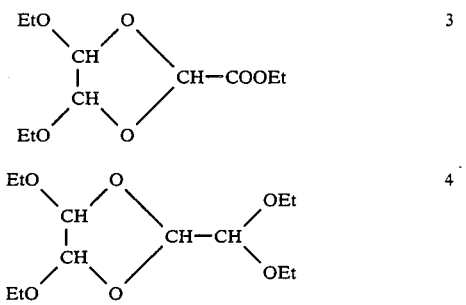

The product 3 was isolated by preparative vapor phase chromatography on a silicone column, then its structure was detected by electronic impact mass spectrometric analyses, on the one hand, and on the other hand, by carbon 13 nuclear magnetic resonance, NMR¹³C. The following values have been obtained:

Mass spectrum, relative abundance as a function of m/e: 234 (M+ 0.1%); 233 (0.7%); 189 (6%); 161 (100%); 103 (37%); 87 (32%); 75 (20%).

RMN¹³C, chemical displacements of the carbons:

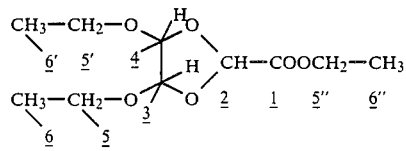

C1, 167.77 ppm; C2, 99.4 ppm; C3 and C4, 103.9 ppm and 104.7 ppm; C5 and C5', 61.7 ppm and 63.8 ppm; C5'', 63.3 ppm; C6, C6', and C6'', 15.0 ppm, 14.8 ppm and 14.1 ppm.

The mixture of products, C, was analyzed by coupling the vapor phase chromatography to the mass spectrometry (electronic impact and chemical ionization by means of ammonia). The results obtained permit to affirm that such mixture is constituted by products of a mass equal to or higher than 234.

The second fraction B is hydrolyzed under high stirring at ambient temperature for 150 minutes in 600 cm³ (0.3 mole) of 0.5N soda.

The obtained emulsion is then washed with ethyl oxide to eliminate the non hydrolyzed products, then the aqueous phase is acidified to pH=1 with sulfuric 4N acid and it is extracted several times with dichloromethane.

The first extraction effected with 3 cm³ of dichloromethane is separated and the following extractions are concentrated dry under vacuum.

There is thus isolated 22.7 g (0.110 mole) of 4,5-diethoxy-1,3-dioxolane-2-carboxylic acid, crystallized in colorless prisms having a melting point of 72°–73° C., not modified by recrystallization in cyclohexane. Such acid has a pKa of 2.1.

The yield is determined to be 33% of the theoretical value as calculated relative to the glyoxal used.

| Microanalysis: | | C (%) | H (%) |
|---|---|---|---|
| C₈H₁₄O₆ | calculated | 46.60 | 6.84 |
| 206.19 | found | 46.7 | 7.0 |

Physical Analyses:
RMN¹H: 10.2 ppm, s, 1H; —COO$\underline{H}$ 5.6 ppm, s, 1H; —C$\underline{H}$—COOH 5.1 ppm, s, 1H; 5.2 ppm, s, 1H; >C$\underline{H}$—C$\underline{H}$< 3.7 ppm, s, 4H; 1.2 ppm, t, 6H; C$\underline{H}_3$ RMN¹³C: 171.7 ppm, $\underline{C}$OOH; 99.1 ppm

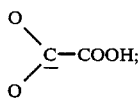

103.9 ppm, 104,6 ppm,

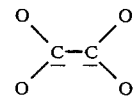

63.9 ppm, 63.7 ppm, $\underline{C}$H₂; 14.9 ppm, 14.7 ppm, $\underline{C}$H₃;

Mass and relative abundance spectrum as a function of m/e: 220 (2%); 207 (2%); 162 (8%); 161 (79%) 132 (5%); 116 (4%); 105 (6%); 104 (7%) 88 (16%); 87 (37%); 76 (36%); 75 (26%) 59 (100%).

To the Applicant's knowledge this product is novel.

EXAMPLE 2

In the same manner as in Example 1 but by replacing ethanol by methanol there is obtained methyl 4,5-dimethoxy-1,3-dioxolane-2-carboxylate, 5, then 4,5-dimethoxy-1,3-dioxolane-2-carboxylic acid, 6.

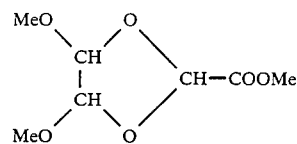

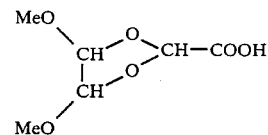

4,5-dimethoxy-1,3-dioxolane-2-carboxylic acid, 5, presents the following chemical displacements:
RMN¹H: 7.0 ppm, s, 1H—COO$\underline{H}$; 5.7 ppm, s, 1H, C$\underline{H}$—COOH; 5.15 ppm, 5.05 ppm, s, 2H,

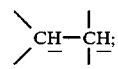

3.4 ppm, s, 6H, CH₃.
RMN¹³C: 170.5 ppm $\underline{C}$OOH; 99.3 ppm,

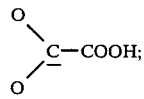

105.0 ppm 105.6 ppm, $\underline{C}$H—$\underline{C}$H; 55.1 ppm, $\underline{C}$H₃.

Methyl 4,5-dimethoxy-1,3-dioxolane-2-carboxylate presents the following chemical displacements:
RMN¹H: 5.5 ppm, s, 1H, C$\underline{H}$—COOM$_e$; 5.0 ppm et 4.9 ppm, s, 2H, C$\underline{H}$—C$\underline{H}$; 3.3 ppm, s, 6H, C$\underline{H}_3$; 3.7 ppm, s, 3H, CH₃.
RMN¹³C: 167.9 ppm, $\underline{C}$OOH; 99.4 ppm, $\underline{C}$H—COOH; 105.1 ppm, 105.7 ppm, —$\underline{C}$H—$\underline{C}$H—; 52.6 ppm, 55.0 ppm, 55.3 ppm, $\underline{C}$H₃.

It will be understood that this invention was only described in a purely explanatory and not at all limitative manner and that any useful modifications thereof can be made without departing from its scope such as defined in the appended claims.

We claim:
1. The products having the general formula (I):

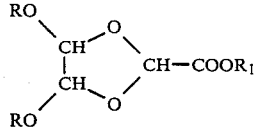

in which R represents an alkyl radical containing from 1 to 4 carbon atoms, and R₁ is selected from the group comprising a hydrogen atom, and alkyl radicals containing from 1 to 4 carbon atoms, in their racemic and optically active forms, as well as the alkaline, alkaline-earth and amine salts, products having the general formula (I) in which R₁ represents a hydrogen atom.

2. Methyl 4,5-dimethoxy-1,3-dioxolane-2-carboxylate, according to claim 1.

3. Ethyl 4,5-diethoxy-1,3-dioxolane-2-carboxylate, according to claim 1.

4. 4,5-dimethoxy-1,3-dioxolane-2-carboxylic acid, according to claim 1.

5. 4,5-diethoxy-1,3-dioxolane-2-carboxylic acid, according to claim 1.

6. A process for preparing the products having the formula (I) according to claim 1, in their racemic or optically active forms, and the alkaline, alkaline-earth and amine salts of said products having the formula (I) in which $R_1$ represents a hydrogen atom, process wherein glyoxylic acid is reacted with an equimolecular quantity of glyoxal in the presence of an alkanol having the formula ROH in which R represents a $C_1$–$C_4$-alkyl radical to obtain a product having the formula (I) in which R and $R_1$, being identical, both represent a $C_1$–$C_4$-alkyl radical.

7. A process for preparing the products having the formula (I) according to claim 1, in their racemic or optically active forms, and the alkaline, alkaline-earth and amine salts of said products having the formula (I) in which $R_1$ represents a hydrogen atom, process wherein glyoxylic acid is reacted with an equimolecular quantity of glyoxal in the presence of an alkanol having the formula ROH in which R represents a $C_1$–$C_4$-alkyl radical to obtain a product having the formula (I) in which R and $R_1$, being identical, both represent a $C_1$–$C_4$-alkyl radical, said reaction being followed by a step of saponification at alkaline pH to obtain a product having the formula (I) in which R represents a $C_1$–$C_4$-alkyl radical and $R_1$ represents a hydrogen atom.

8. A process for preparing the products having the formula (I) according to claim 1, in their racemic or optically active forms, and the alkaline, alkaline-earth and amine salts of said products having the formula (I) in which $R_1$ represents a hydrogen atom, process wherein glyoxylic acid is reacted with an equimolecular quantity of glyoxal in the presence of an alkanol having the formula ROH in which R represents a $C_1$–$C_4$-alkyl radical to obtain a product having the formula (I) in which R and $R_1$, being identical, both represent a $C_1$–$C_4$-alkyl radical, said reaction being followed by a step of saponification at alkaline pH to obtain a product having the formula (I) in which R represents $C_1$–$C_4$ alkyl radical and $R_1$ represents a hydrogen atom, further comprising a step of salification or esterification in neutral or alkaline medium.

* * * * *